United States Patent [19]

Okamoto et al.

[11] Patent Number: 5,049,587

[45] Date of Patent: Sep. 17, 1991

[54] OPTHALMIC-SOLUTION FOR INTRAOCULAR PRESSURE ADJUSTMENT

[75] Inventors: Taira Okamoto; Motoyuki Yajima, both of Otsu, Japan

[73] Assignee: Basotherm GmbH, Biberach an der Riss, Fed. Rep. of Germany

[21] Appl. No.: 341,408

[22] Filed: Apr. 21, 1989

[30] Foreign Application Priority Data

Apr. 21, 1988 [JP] Japan .................................. 63-99128
Nov. 2, 1988 [JP] Japan ............................... 63-278317

[51] Int. Cl.$^5$ ......................................... A61K 31/135
[52] U.S. Cl. .................................... 514/653; 514/913
[58] Field of Search ............................... 514/466, 653

[56] References Cited

U.S. PATENT DOCUMENTS 4,119,710 10/1978 Engelhardt et al. ................. 514/446
4,214,001 7/1980 Engelhardt et al. ................. 514/482

Primary Examiner—Stanley J. Friedman
Assistant Examiner—Zohyeh A. Fay
Attorney, Agent, or Firm—David E. Frankhouser; Alan R. Stempel; Mary-Ellen M. Timbers

[57] ABSTRACT

Disclosed are novel opthalmic solutions useful for the treatment of ocular hypertension and glaucoma. These contain mabuterol as a preferred active ingredient.

3 Claims, 13 Drawing Sheets

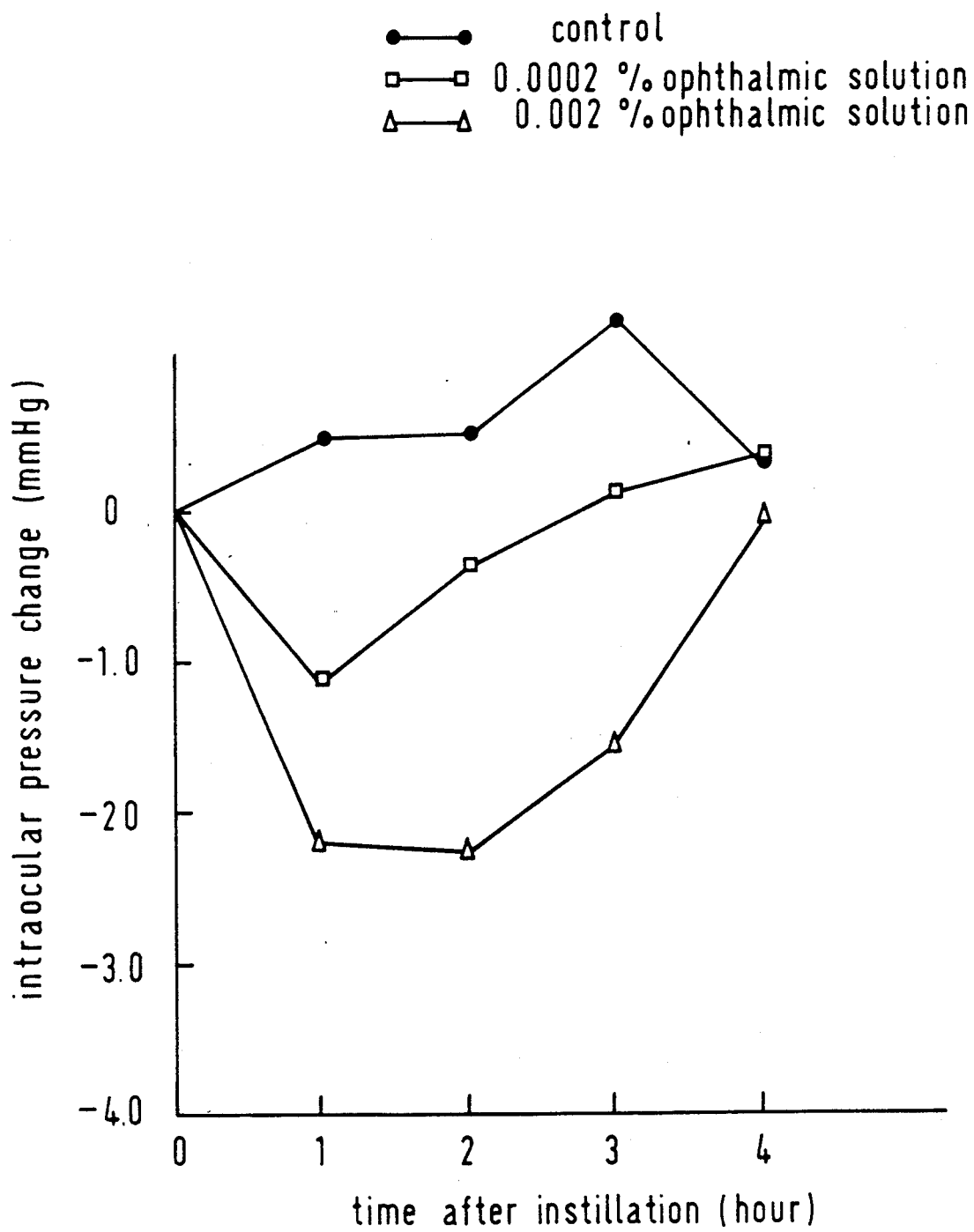

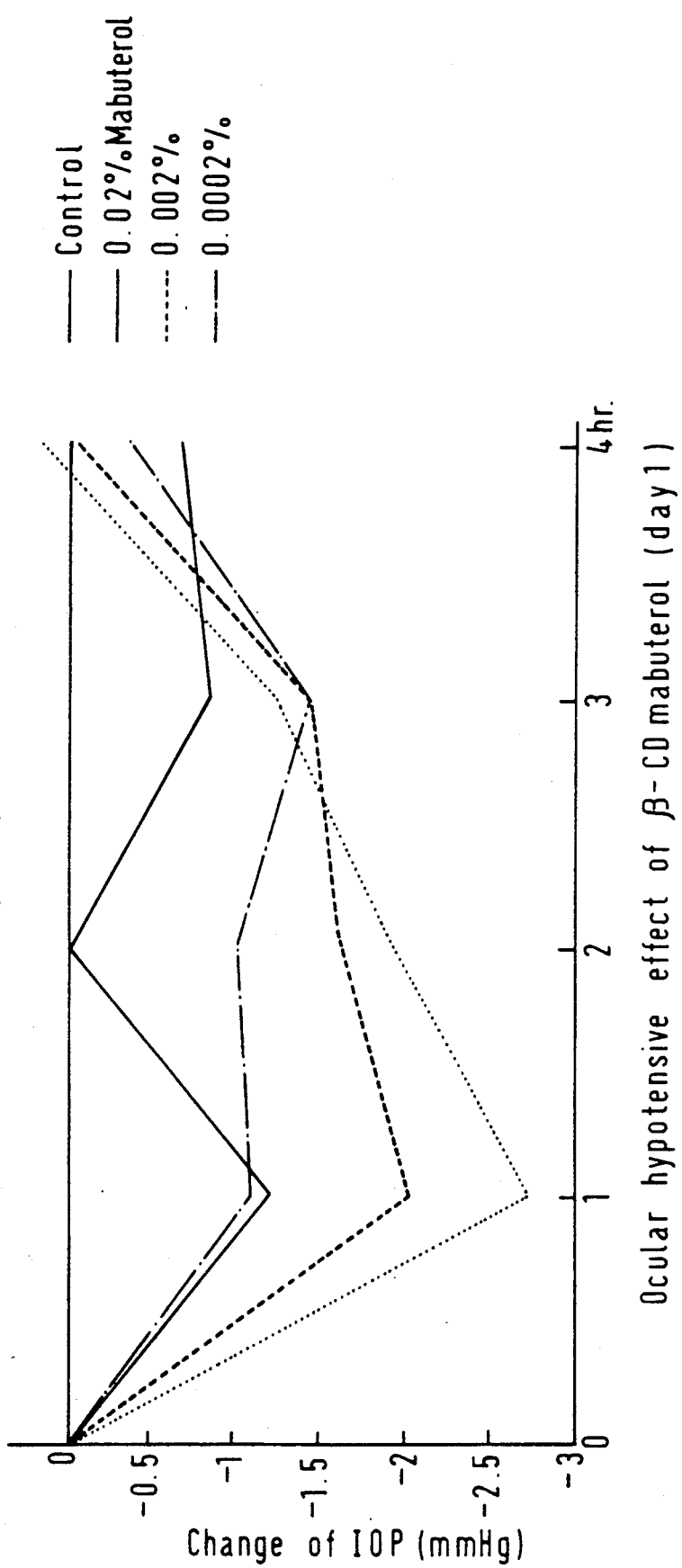

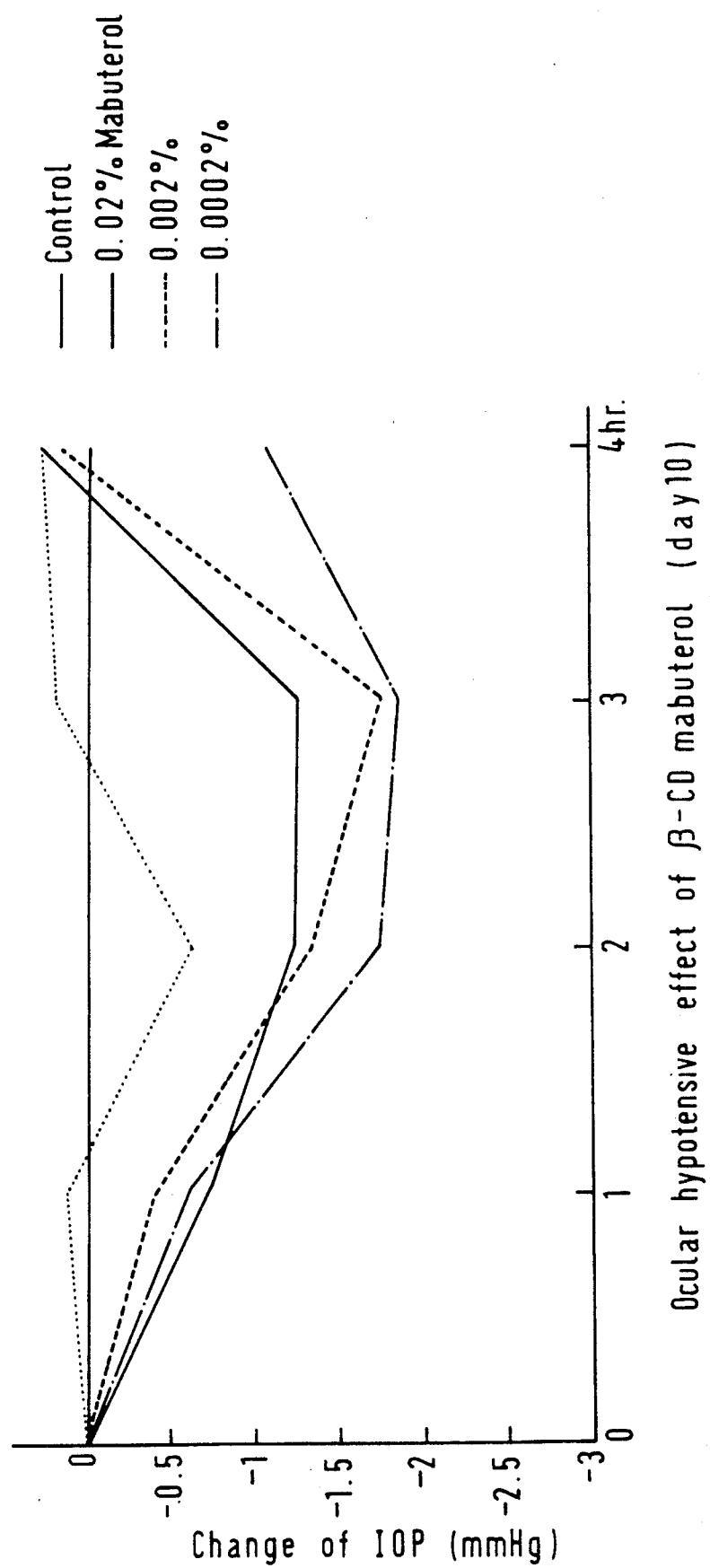

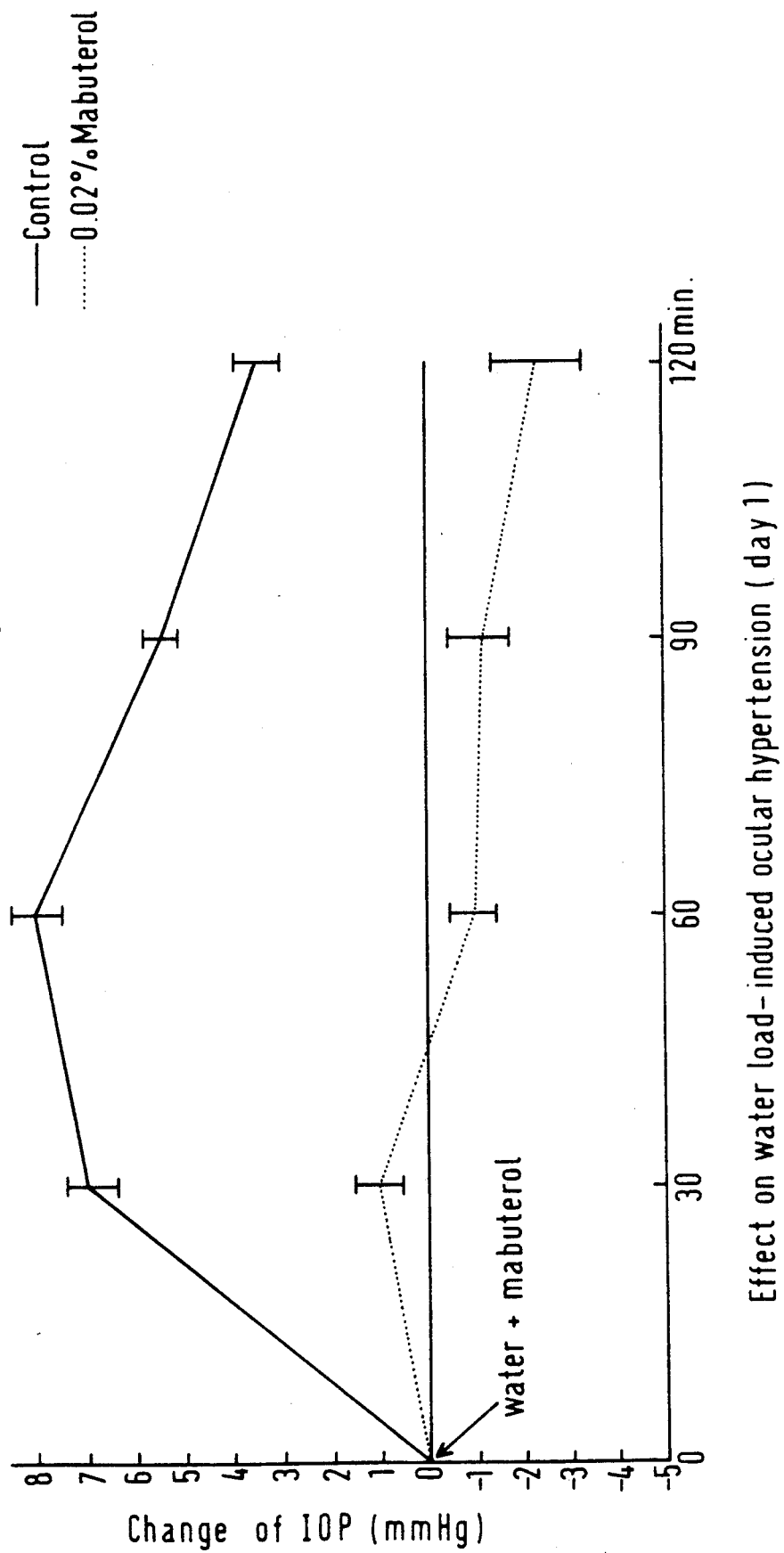

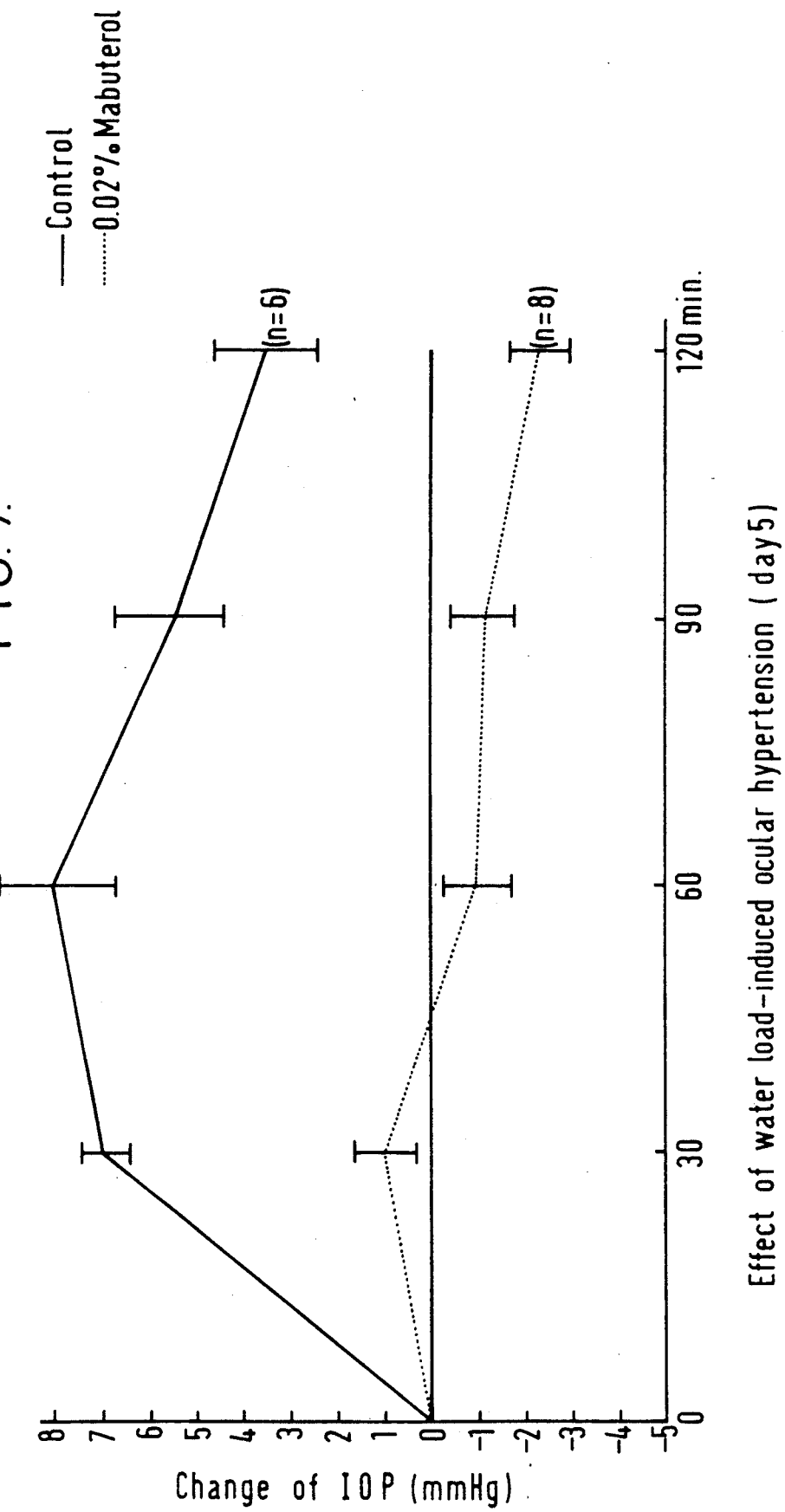

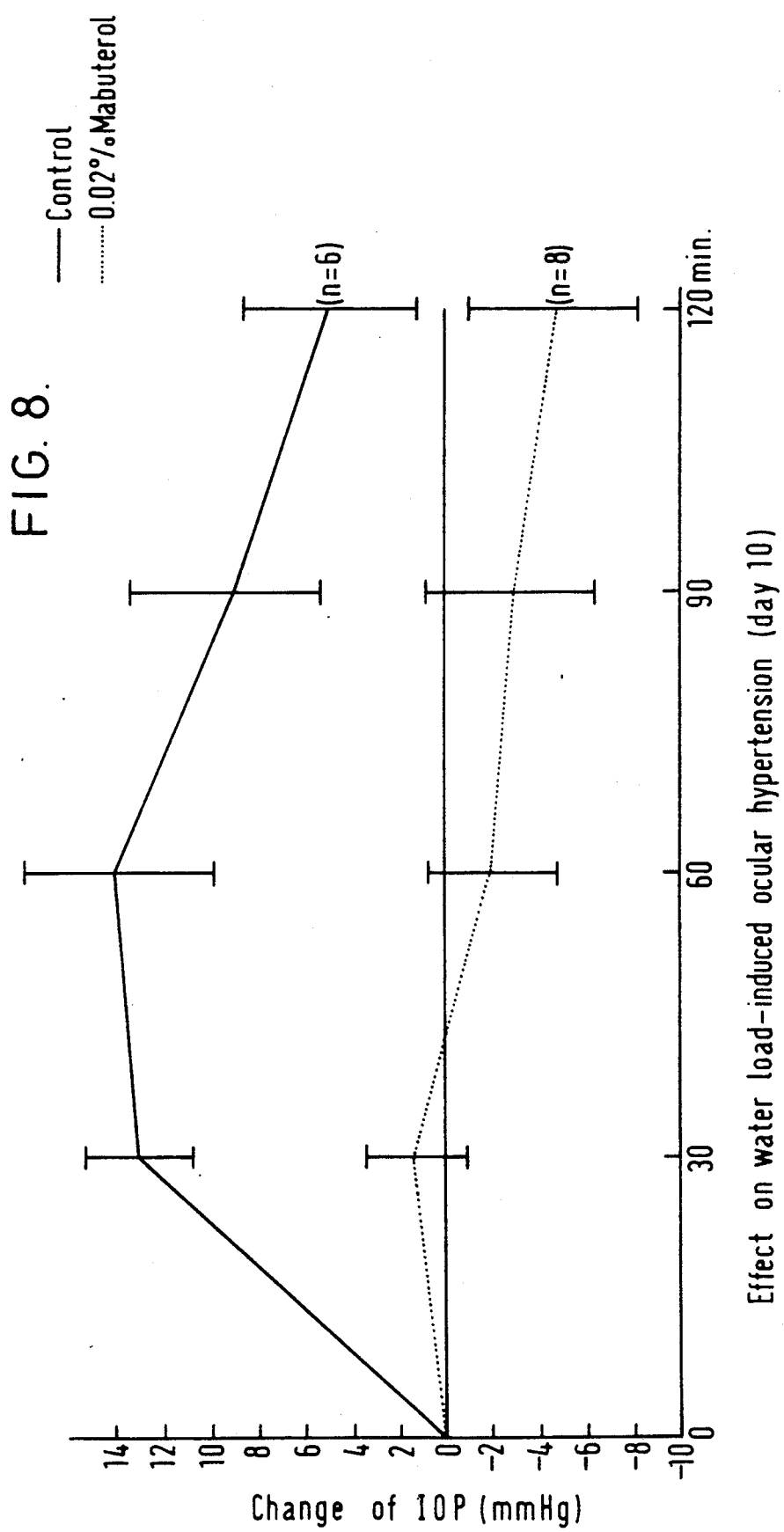

Effect on water load-induced hypertension
(5 days of instillation and loading)

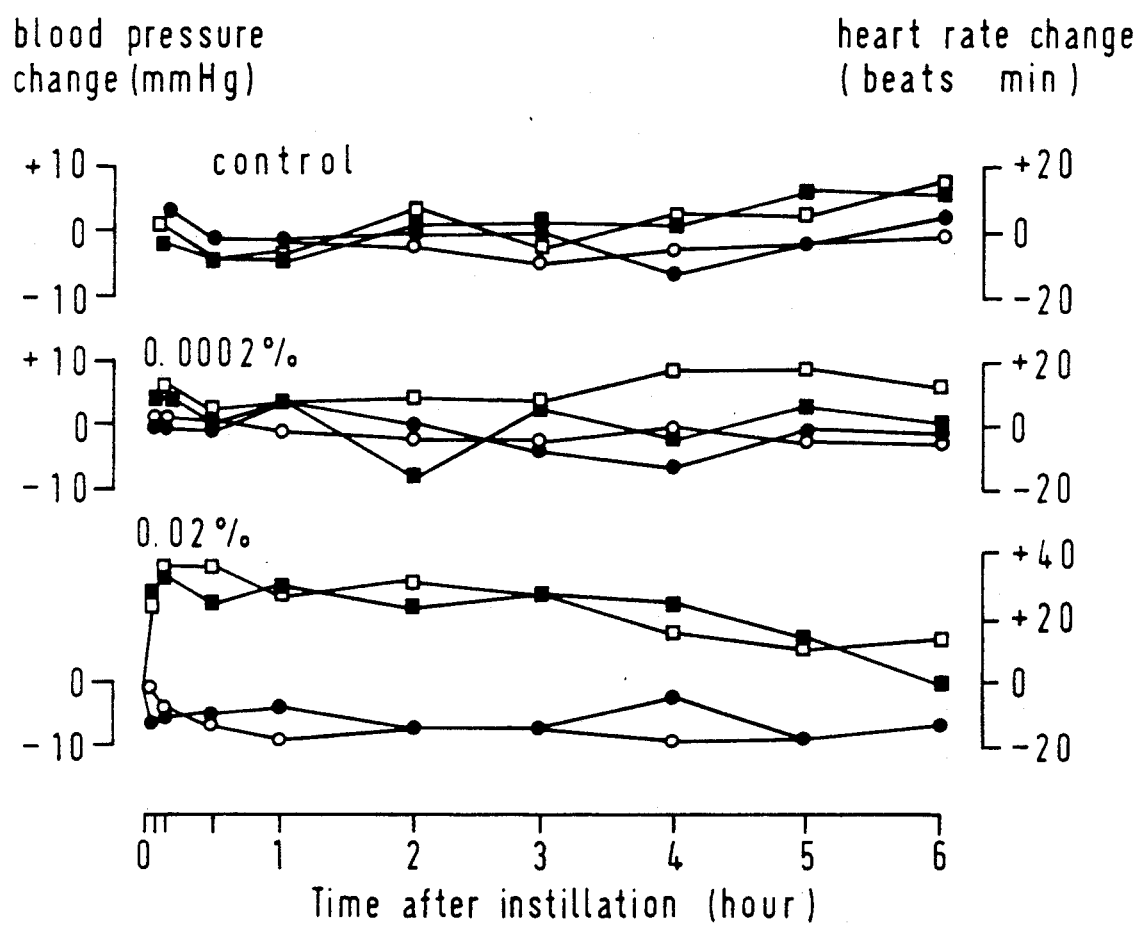

OPHTHALMIC-SOLUTION FOR INTRAOCULAR PRESSURE ADJUSTMENT

DETAILED EXPLANATION OF THE INVENTION

Technical field of the invention

The present invention relates to a novel ophthalmic solution for intraocular pressure adjustment, and more particularly to an ophthalmic solution for intraocular pressure adjustment useful for treatment of ocular hypertension and glaucoma.

Prior art and problems to be solved by the invention

Hitherto, a pilocarpine ophthalmic solution has been employed as an intraocular pressure adjusting agent for use in the treatment of ocular hypertension and glaucoma. It is known however, that whilst the pilocarpine ophthalmic solution decreases the intraocular pressure, it also acts on the sphincter of the pupil and ciliary body and has side effects such as visual darkness due to miosis, disorder of accomodation and conjunctival injection. Such side effects give rise to serious problems, particularly for persons working in communication and transportation. Also, in case of a middleaged cataract patient, the side effects increase visual disorder due to miosis. From the viewpoint of these defects, there is a need for the development of intraocular pressure adjusting agents for treating ocular hypertension and glaucoma to replace the pilocarpine ophthalmic solution.

An epinephrine ophthalmic solution was developed on the basis of such a need, but it has side effects such as conjunctival congestion, pain in eye-brow region or allergic blepharoconjunctivitis and in some cases, it brings about an intraocular pressure rise due to mydriasis. Therefore, the epinephrine ophthalmic solution is not widely used. Also, it has been attempted clinically to use surface anesthetics and psychotropic drugs to produce a decrease of intraocular pressure of the glaucoma eye, but such drugs have not been put into practical use.

It has recently been observed that various β-receptor blocking agents decrease intraocular pressure when orally administered; subsequently it was found, that bupranolol, timolol, and the like among the β-receptor blocking agents show the above effect also in topical solutions.

However, it is difficult to use them clinically as ophthalmic solutions due to their strong irritating effects. Also, phthalmic solutions containing β-receptor blocking agents are contraindicated, since asthma is induced when they are applied to asthmatic patients. In some cases, bradycardia is caused.

It is an object of the present invention to provide an ophthalmic solution for intraocular pressure adjustment, which shows no miosis action as is the case for the pilocarpine ophthalmic solutions, and which is not accompanied by a risk that they are contraindicated for asthmatic patients or that bradycardia is caused as is the case when ophthalmic solutions containing β-receptor blocking agents are involved; and which has a curative effect when applied in small quantities due to their strong intraocular pressure reducing activity.

Means to solve the problems

The present invention relates to an ophthalmic solution for intraocular pressure adjustment comprising as an active ingredient a compound of formula I

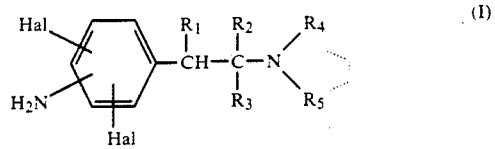

wherein each Hal is chlorine or bromine, $R_1$ is hydrogen or hydroxyl, $R_2$ and $R_3$ are each hydrogen or alkyl of 1 to 4 carbon atoms, and $R_4$ and $R_5$ are each hydrogen, lower alkyl, lower alkenyl, lower alkinyl, hydroxy-lower alkyl, lower alkoxy-lower alkyl, di-lower alkyl-amino-lower alkyl, cycloalkyl, phenyl, benzyl or adamantyl; or, together with each other and the nitrogen atom to which they are attached, pyrrolidino, lower alkyl-pyrrolidino, piperidino, lower alkyl-piperidino, piperazino, N'-lower alkyl-piperazino, morpholino, lower alkylmorpholino, hexamethyleneimino, lower alkyl-hexamethyleneimino, camphidino or lower alkyl-camphidino; or a non-toxic, pharmacologically acceptable acid addition salt thereof, or a racemic mixture or optically active antipode of a compound of formula II

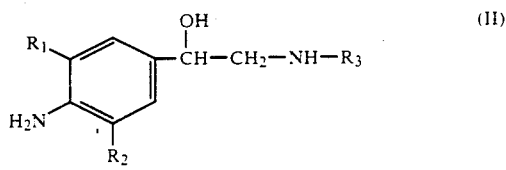

wherein $R_1$ is hydrogen, fluorine, chlorine, bromine, iodine or cyano, $R_2$ is fluorine, trifluoromethyl, nitro or cyano, and $R_3$ is alkyl of 3 to 5 carbon atoms, hydroxyalkyl of 3 to 5 carbon atoms, cycloalkyl of 3 to 5 carbon atoms, 1-(3,4-methylenedioxy-phenyl)-2-propyl or 1-(p-hydroxy-phenyl)-2-propyl, or a non-toxic, pharmaceutically acceptable acid addition salt thereof, or a compound of the formula III

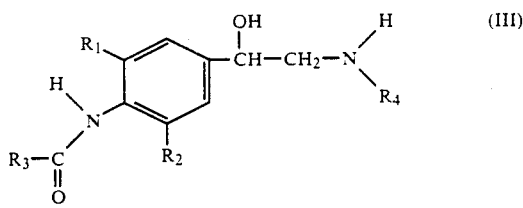

wherein $R_2$ is hydrogen, halogen or cyano, $R_2$ is fluorine, cyano, trifluoromethyl, nitro or alkyl of 1 to 4 carbon atoms, $R_3$ is alkoxy of 1 to 5 carbon atoms, alkenyloxy of 2 to 5 carbon atoms, aryloxy of 6 to 10 carbon atoms, aralkoxy of 7 to 11 carbon atoms or $-NR_5R_6$ where $R_5$ and $R_6$ are each hydrogen, alkyl of 1 to 5 carbon atoms, alkenyl of 2 to 5 carbon atoms, aryl of 6 to 10 carbon atoms or aralkyl of 7 to 11 carbon atoms, and $R_4$ is cycloalkyl of 3 to 5 carbon atoms or alkyl of 3 to 5 carbon atoms, or a non-toxic, pharmacologically acceptable acid addition salt thereof, preferably 1-(4'-amino-3',5'-dichlorophenyl)-2-(tert.butylamino)-ethanol-(1), especially preferably 1-(4'-amino-3'-chloro-5'-trifluoromethyl-phenyl)-2-tert.butylaminoethanol (hereinafter referred to as "mabuterol") or their non-toxic, pharmaceutically acceptable acid addition salts.

The compounds of formula I exhibit bronchodilating, analgesic, sedative, antipyretic, antiphlogistic and antitussive activities as well as enhance blood circulation in warmblooded animals; the compounds have been known by U.S. Pat. No. 3,536,712. For instance, the compound 1-(4'-amino-3',5'-dichloro-phenyl)-2-(tert.butylamino)-ethanol-(1), known as clenbuterol, exhibits especially bronchodilating properties.

The compounds of formula II exert bronchospasmolytic activities and are described by U.S. Pat. No. 4,119,710; the compounds of formula III show bronchospasmolytic and antiasthmatic activities and are described by U.S. Pat. No. 4,214,001. However, there has, hitherto, been no literature suggesting that these compounds of formulae I to III exert the pharmacological action as disclosed in the present invention.

The pharmacological action of the compounds of formulae I to III as disclosed in the present invention has been found for the first time by the present inventors. Especially Mabuterol, which is 1-(4'-amino-3'-chloro-5'-trifluoromethyl-phenyl)-2-tert.butylaminoethanol and its non-toxic, pharmacologically acceptable acid addition salts, which is disclosed in U.S. Pat. No. 4,119,710, shows excellent results with regard to the new activity which is disclosed in the present invention.

In the ophthalmic solution for intraocular pressure adjustment (hereinafter referred to as "ophthalmic solution") of the present invention, the compounds of formulae I to III, especially mabuterol as the active ingredients might be employed in their free form or as a salt thereof. It is preferable to use the compounds, e.g. mabuterol, as ophthalmologically acceptable salts in aqueous solution, since such formulations bring the least pain and inconvenience.

The formulations are not limited to an aqueous solution, and the ophthalmic solution can be employed in any form such as an oily collyrium, a sustained release collyrium or a suspension. Moreover, the ophthalmic solution can be in the form of crystals capable of dissolving or suspending with a suitable solvent when applying it.

Examples for the salts of the compounds of formulae I to III, e.g. of mabuterol, are, for instance, inorganic acid salts such as phosphoric acid salt, hydrochloric acid salt, sulfuric acid salt and hydrobromic acid salt, organic acid salts such as citric acid salt, maleic acid salt, fumaric acid salt, tartaric acid salt and malic acid salt, and the like. The hydrochlorid acid salt is particularly preferred from viewpoints of economy and stability of the ophthalmic solution.

When an aqueous solution is prepared by employing the above mentioned salts, e.g. of mabuterol, as the active ingredients, it is preferable and convenient that the salts are dissolved in an aqueous solvent such as water, physiological saline or phosphate buffer solution. Also non-aqueous solvents for the preparation of an ophthalmic solution can be used.

In the case of preparing a non-aqueous ophthalmic solution this can be prepared in a manner known per se employing the compounds of formulae I to III, e.g. mabuterol, or the salts thereof as the active ingredient.

It is preferred that the ophthalmic solution of the present invention is administered once or twice daily in a dosage of $1 \times 10^{-6}$ to 2,0 mg of the active ingredient per day, to adjust intraocular pressure. It is especially preferred that the ophthalmic solution is administered once or twice daily in a dosage of $5 \times 10^{-5}$ to $5 \times 10^{-3}$ mg per day, especially when mabuterol is used, from the viewpoints of intraocular pressure reduction and the duration of the effect. Further, it is preferred that the concentration of the active ingredient in the ophthalmic solution is from 0,0001 to 4,0 % (% by weight, hereinafter the same) from the viewpoint of adjusting the intraocular pressure, more preferably from 0,0002 to 2,0 %; this applies especially to mabuterol.

The ophthalmic solution of the present invention is usually used in a dose of about 1 to 2 drops (35 to 70 μl) to give satisfactory duration of activity and at this dosage shows a remarkable effect in decreasing intraocular pressure. In addition to the above mentioned active ingredients, the ophthalmic solution of the present invention suitably may contain additives usually used in the ophthalmic solutions such as preservative agents e.g. chlorobutanol, sodium dehydroacetic acid, benzalkonium chloride and methyl p-hydroxybenzoate, buffering agents e.g. boric acid and borax, viscosity-inducing agents e.g. methyl cellulose (MC), sodium carboxymethyl cellulose (CMC-Na) and chondroitin sulfuric acid and other additives e.g. sodium chloride and polyvinyl alcohol.

When storing the ophthalmic solution of the present invention, the solution is stored in a refrigerator shielding it from light or in a dark cold place.

The ophthalmic solution of the present invention is more specifically described and explained by means of the following examples. It is to be understood that the present invention is not limited to the examples.

EXAMPLE 1

Mabuterol hydrochloride was dissolved in phosphate buffer solution of pH 6,7 to give an ophthalmic solution containing 0,0002 %, 0,002 %, 0,02 %, 0,2 % or 2 % of mabuterol hydrochloride (hereinafter referred to as "0,0002 % ophthalmic solution", "0,002 % ophthalmic solution", "0,02 % ophthalmic solution", "0,2 % ophthalmic solution" and 2 % ophthalmic solution" respectively).

Each of the obtained ophthalmic solutions was then subjected to the following test:

Test Example 1 (effect on the decrease of intraocular pressure of normal eyes of the rabbit)

Experimental animals

Thirty male normal adult white rabbits having a body weight of 2,5 to 3,5 kg (Japanese white native species, 6 to 13 months old) were divided into 6 groups. In each group, 10 eyes of 5 rabbits were used.

Apparatus for measurement

As the apparatus for measurement, an air tonometer (Pneumatic tonometer made by Alcon Laboratories, INC., hereinafter referred to as "PTG") was used. Calibration was carried out in every measurement, and the measurements were carried out every 1 hour by the same man at the same time.

Method to administer using agents

There were exactly measured 50 μl of 0,0002 %, 0,002 %, 0,02 %, 0,2 % or 2 % ophthalmic solution with a micropipette, and the solution was applied to all 10 eyes of 5 rabbits. A phosphate buffer solution having pH 6,7 was applied to all 10 eyes of 5 rabbits constituting a control group in the same manner as above.

Test method

After anesthetising the rabbits by instilling 0,4 % of oxyprocaine hydrochloride, intraocular pressures of both eyes of the rabbit were measured three times by using PTG, before the application of the ophthalmic solution and at intervals of 1 hour during 5 hours after application.

Measurement results
Effect on intraocular pressure in relation to the dosage of mabuterol By the above-mentioned measurements a decrease of intraocular pressure was found for ophthalmic solutions containing not less than 0,0002 % mabuterol hydrochloride. The decreases of intraocular pressure found after 1 hour after application were 7,0±0,63 mmHg for the 2 % ophthalmic solution, 5,2±0,5 mmHg for the 0,2 % ophthalmic solution, 3,5±1,06 mmHg for the 0,02 % ophthalmic solution, 2,2±1,05 mmHg for the 0,002 % ophthalmic solution and 1,13±0,48 mmHg for the 0,0002 % ophthalmic solution.

FIG. 1 is a graph showing a relation between the concentrations of mabuterol in the ophthalmic solution (the concentration of the ophthalmic solution) and the intraocular pressure change 1 hour after the application. Effect on intraocular pressure of mabuterol with the lapse of time When the 0,0002 % ophthalmic solution was used, the intraocular pressure 1 hour after the application had decreased by about 1,0 mmHg, thereafter the intraocular pressure gradually increased to the value existing before the treatment. It was found that the intraocular pressure at 4 hours after the application showed the same pressure as the intraocular pressure of the control group. The remarkable effect on decrease of intraocular pressure by mabuterol disappeared after 4 hours from the instillation when using mabuterol hydrochloride solutions in low concentrations (0,0002 % and 0,002 %), and it disappeared after 5 hours from application when using mabuterol hydrochloride solutions in middle and high concentrations (0,02 %, 0,2 % and 2,0 %).

FIG. 2a and FIG. 2b are graphs showing a relation between time after instillation and intraocular pressure.

EXAMPLE 2

Mabuterol hydrochloride was dissolved in phosphate buffer solution having a pH of 6,7 to adjust a concentration thereof to $10^{-4}$ g/ml The obtained mabuterol hydrochloride solution was used in the following test:

Test Example 2 (influence on dog's heart vessel system)

The mabuterol hydrochloride solution obtained according to Example 2, having a concentration of $10^{-4}$ g/ml, was intravenously administered into the cervical vein of a male dog having a body weight of about 15 kg (beagle, about 13 months old), and the carotid artery pressure was measured using a pressure transducer. FIG. 3 is a sketch of a part of a chart showing the change in carotid artery pressure by time after administration, recorded in a polygraph by the transducer.

The arrow A shows the point of time when the mabuterol hydrochloride solution was administered.

About 30 seconds after the administration of the mabuterol hydrochloride, the mean blood pressure decreased by 15 mmHg. From this result, it can be understood that, though the ophthalmic solution of the present invention decreases the intraocular pressure to a remarkable degree, the blood pressure is affected only slightly.

EXAMPLE 3

An ophthalmic solution having a pH of 6,7 was prepared by dissolving 0,44 g of sodium chloride in 80 ml of a solution prepared by dissolving of 0,303 g of anhydrous potassium dihydrogenphosphate and 0,794 g of disodium hydrogenphosphate (dodecahydrate) in sterile purified water, adding 2 mg of mabuterol hydrochloride and 0,019 g of propyl p-hydroxybenzoate to the solution, adding sterile purified water thereto to adjust the total amount to 100 ml, and sterilising through a filter. The solution contains 0,002 % mabuterol-hydrochloride (w/v). Ophthalmic solutions containing 0,0002 %, 0,02 % and 2 % mabuterol-hydrochloride were prepared accordingly (see the following Table 1).

TABLE 1

| Component (%) | 0,0002% ophthalmic solution | 0,002% ophthalmic solution | 0,02% ophthalmic solution | 2% ophthalmic solution |
|---|---|---|---|---|
| *1 | 0,0002 | 0,002 | 0,02 | 2 |
| *2 | 2 | 2 | 2 | 2 |
| *3 | 0,61 | 0,61 | 0,61 | 0,61 |
| *4 | 0,007 | 0,007 | 0,007 | 0,007 |
| *5 | proper quantity | proper quantity | proper quantity | proper quantity |

Note
*1: mabuterol-hydrochloride
*2: sodium hydrogenphosphate
*3: anhydrous sodium dihydrogenphosphate
*4: benzalkoniumchloride
*5: sterile purified water ad 100 ml According to the prescriptions in Table 2, 0,0002 %, 0.002 % and 0,02 % ophthalmic solutions containing β-cyclodextrin were prepared (pH 7).

TABLE 2

| Component (%) | 0,0002% ophthalmic solution | 0,002% ophthalmic solution | 0,02% ophthalmic solution |
|---|---|---|---|
| *1 | 0,0002 | 0,002 | 0,02 |
| *2 | 0,735 | 0,735 | 0,735 |
| *3 | 2,4 | 2,4 | 2,4 |
| *4 | 0,61 | 0,61 | 0,61 |
| *5 | proper quantity | proper quantity | proper quantity |

Note
*1: mabuterol-hydrochloride
*2: β-cyclodextrin
*3: sodium hydrogenphosphate
*4: anhydrous sodium dihydrogenphosphate
*5: sterile purified water ad 100 ml

EXAMPLE 4

Stability tests of pharmaceutical preparations

Phosphate buffer solutions (pH 6,7), containing 0,0002 %, 0,002 %, 0.02 % or 2 % mabuterol-hydrochloride according to Example 1 were filled in 5 ml-vessels made of polypropylene and were stored at room temperature, 5° C. and 40° C.

With the samples stored at room temperature and at 5° C. on the fourteenth day, at 40° C. on the twentieth day, the following measurements of pH-value, of the osmotic pressure and of content, besides observations of appearance and of formation of cleavage products were carried out according to the following conditions:

pH: pH meter (F-7 type, made by Horibasha),
osmotic pressure (mOsm/kg): osmometer OSM-STAT-OM-6020 (made by Kyoto Daiichi Kagakusha),
appearance: observation by eyes, content (%): spectrophotometer (200-10 types spectrophotometer, made by Hitachi, Ltd.),
confirmation: TLC
  thin-layer plate (Kieselgel 60F254, made by Merck, 20 cm)
  solvent for development (chloroform/ethanol/glacial acetic acid (8:1:1)).

In an ophthalmic solution the concentration of which is not more than 0,02 % mabuterol-hydrochloride, no change was observed in each value measured when stored at room temperature, 5° C. and 40° C. In a 2 % ophthalmic solution, a change of appearance was observed at room temperature, 5° C. and 40° C. After storing at 40° C., a decrease of content of the active substance and cleavage products were observed.

In Table 3, the results of stability tests are shown being carried out at the fourtieth day with ophthalmic solutions according to Example 1 when stored at 5° C. and at room temperature. In Table 4, the results of stability tests are shown being carried out on the twentieth day with ophthalmic solutions according to Example 1 when stored at 40° C.

tained action, was examined in rabbits with normal as well as elevated IOP:

Materials and Methods

Composition of the eye drop

| Mabuterol-HCl | 0,02 (W/W) | 0,002 (W/W) | 0,0002 (W/W) | 0 (W/W) |
|---|---|---|---|---|
| β-Cyclodextrin | 0,735% | | | |
| Na$_2$HPO$_4$.12H$_2$O | 2,4% | | | |
| NaH$_2$PO$_4$ | 0,61% | | | |
| pH: 7 | | | | |
| osmotic pressure ratio: ca. 0,9 | | | | |
| β-CD inclusion: ca. 47% | | | | |

Normal IOP

50 μl of mabuterol β-CD eye drop (0,02 %, 0,002 %, 0,0002 %) were administered into both eyes of 4 male albino rabbits once daily for 17 days. To a control group of 4 animals a phosphate buffer solution (pH 7) containing β-CD was administered in the same way.

TABLE 3

| Storage condition and term Test item | | pH | Osmotic pressure | Appearance | Content | Confirmation |
|---|---|---|---|---|---|---|
| | | | | Starting point of the stability test | | |
| Mabuterol-hydrochloride content in sample solution | 0% | 6,89 | 242 | clear colorless | — | — |
| | 0,0002% | 6,89 | 241 | " | 98,0 | single spot |
| | 0,002% | 6,88 | 240 | " | 106,0 | " |
| | 0,02% | 6,88 | 237 | " | 97,6 | " |
| | 2,0% | 6,81 | 356 | " | 98,5 | " |
| | | | | After 40 days 5° C. | | |
| Mabuterol-hydrochloride content in sample solution | 0% | 6,90 | 245 | no change | — | — |
| | 0,0002% | 6,88 | 243 | " | 101,5 | no change |
| | 0,002% | 6,87 | 241 | " | 102,8 | " |
| | 0,02% | 6,87 | 241 | " | 99,6 | " |
| | 2,0% | 6,79 | 359 | *1 | 101,5 | " |
| | | | | After 40 days Room temperature | | |
| Mabuterol-hydrochloride content in sample solution | 0% | 6,87 | 246 | no change | — | — |
| | 0,0002% | 6,87 | 242 | " | 103,1 | no change |
| | 0,002% | 6,87 | 243 | " | 105,7 | " |
| | 0,02% | 6,87 | 241 | " | 99,6 | " |
| | 2,0% | 6,80 | 360 | *1 | 101,5 | " |

Note:
*1 Slight white muddiness is found when a sample solution is storaged at 5° C. or at room temperature.

TABLE 4

| Storage condition and term Test item | | After 20 days 40° C. | | | | |
|---|---|---|---|---|---|---|
| | | pH | Osmotic pressure | Appearance | Content | Confirmation |
| Mabuterol-hydrochloride content in sample solution | 0% | 6,89 | 246 | clear colorless | — | — |
| | 0,0002% | 6,88 | 244 | " | 101,5 | single spot |
| | 0,002% | 6,88 | 242 | " | 105,6 | " |
| | 0,02% | 6,88 | 241 | " | 99,6 | " |
| | 2,0% | 6,71 | 325 | *1 | 54,6 | cleavage product *2 |

Note:
*1: There are found sedimented white foreign materials which are about azuki-bean-size
*2: Rf-value of 0,2 was found besides a Rf-value of 0,5 which is equal to the Rf-value of mabuterol

EXAMPLE 5

As reported in Example 1, mabuterol.HCl remarkably reduced normal intraocular pressure (IOP) in rabbits, and the effect gradually diminished by repeated administration.

In the following experiments, the drug, which was included in β-cyclodextrin (β-CD) to provide a sus- On days 1, 10 and 17, IOP was measured as described in the previous examples.

Water load-induced ocular hypertension 20 ml of water (37° C.) were orally administered to rabbits. 50 μm of the mabuterol β-CD eye drop was applied to both eyes of the rabbits immediately after water load.

In Experiment I, the animals received the eye drops once daily for 10 days and on days 1, 5 and 10 IOP was measured after water load. In Experiment II, the animals were treated and water loaded daily for 10 days, and on days 1, 5 and 10 IOP was measured.

Results

Effect on normal IOP

On day 1, the 0,02 % and 0,002 % mabuterol solution but not the 0,0002 % mabuterol solution produced a significant fall in IOP. On days 10 and 17, the drug did not reduce IOP at any concentration examined (FIGS. 4 and 5).

As particularly shown in FIG. 4, it was found that 0,0002 %, 0,002 % and 0,02 % mabuterol-hydrochloride ophthalmic solutions showed significant decreases of intraocular pressure in comparison to the control group. The decreases of intraocular pressure after 1 hour from the administration were $2,00 \pm 0,42$ mmHg in the 0,002 % mabuterol-hydrochloride ophthalmic solution, and $2,63 \pm 0,75$ mmHg in the 0,02 % mabuterol-hydrochloride ophthalmic soltuion. Though a tendency of decrease of intraocular pressure with a 0,0002 % mabuterol-hydrochloride ophthalmic solution was found, this result is not significant.

FIG. 4 is a graph showing a relation between the time after administration and the intraocular pressure change.

Effect on elevated IOP

Experimental animals

Eight male normal adult white rabbits having a body weight of 2,8 to 3,9 kg (Japanese white native species, 7 to 8 months old) were divided into 2 groups. In each group, 8 eyes of 4 rabbits were used.

Apparatus for measurement

As the apparatus for measurement, a PTG made by Alcon Laboratories, Inc., was used. The calibration was carried out for each measurement, and the measurements were carried out every 30 minutes by the same man at the same time.

Loading with water

The loading with water was carried out by orally administering of 20 ml of warm water (about 37° C.) to eight rabbits.

Method of administration

Exactly 50 μl of 0,02 % mabuterol-hydrochloride ophthalmic solution were administered to 8 eyes of 4 rabbits, simultaneously to the loading with water. As a control group, a phosphate buffer solution having a pH of 7,0 which contained β-cyclodextrin was administered to 8 eyes of 4 rabbits in the same manner as above.

After administering the solution resp. solutions the intraocular pressures of both eyes of the rabbit were measured two times by using PTG at intervals of 30 minutes over 2 hours. The 0,02 % mabuterol-hydrochloride ophthalmic solution was administered on each day during ten days, the loading with water was carried out at day one, day five and day ten.

a) Results of Experiment I

IOP in controls increased by about 10 mmHg after water load, whereas it was virtually unchanged in those animals receiving the drug indicating that a water load-induced rise in IOP was significantly inhibited by the drug (two way analysis of variance) (FIG. 6). Similar results were obtained on days 5 and 10 (FIGS. 7 and 8).

b) Results of Experiment II

The eye drops significantly inhibited a water load-induced increase in IOP on days 1, 5 and 10 (FIGS. 9 and 10).

EXAMPLE 6

Mabuterol-hydrochloride was dissolved in a physiological saline to give an ophthalmic solution containing 0,0002 % or 0,02 % of the mabuterol-hydrochloride (hereinafter referred to as "0.0002 % mabuterol physiological saline" and "0,02 % mabuterol physiological saline" respectively).

These physiological salines were then subjected to the following tests:

Test to show the influence on blood pressure, heart rate and electrocardiogram

Experimental animals

Fifteen male normal adult white rabbits having a body weight of 3,2 to 3,5 kg (Japanese white native species, 7 to 10 months old) were divided into 3 groups. In each group, 10 eyes of 5 rabbits were used.

Apparatus for measurement

For the measurements of blood pressure was used a pressure transducer (trade-name: MP-4T, made by Nippon Koden Kogyo K.K.), for recording the heart rate and the electrocardiogram were used a tachometer in connection with a polygraph (trade-name: RT-5, mady by Nippon Koden Kogyo K.K.). Measurements were carried out every hour by the same man at the same time.

Method for administration

50 μl of a 0.0002 % or 0,02 % mabuterol-hydrochloride containing physiological saline were exactly measured with a micropipette; the solution was administered to 10 eyes of 5 rabbits. To a control group only physiological saline was administered to 10 eyes of 5 rabbits in the same manner as above.

Test method

Blood pressure, heart rate and electrocardiogram were measured 5 and 10 minutes after the administration and, then, at intervals of 1 hour, over the length of 6 hours. The administration was carried out once a day during 8 days. The measurement was carried out on the first day and the eighth day.

Measurement results

At the first day, though the blood pressure had a tendency to decrease after administraiotn of a 0,002 % mabuterol-hydrochloride solution, a significant difference could not be observed. However, a significant increase of the heart rate was found. At the eighth day the same result as at the first day was observed. As to electrocardiogram, there was no remarkable change observable neither at the first day nor at the eighth day. These results show that the ophthalmic solutions containing mabuterol do not remarkably influence blood pressure (shown in FIGS. 11 and 12).

FIGS. 11 and 12 are graphs showing a relation between time after administration of intraocular pressure and between time after administration and heart rate at the first day and the eight day respectively. FIG. 13 is a graph showing the results according to FIGS. 11 and 12 for each of the ophthalmic solutions used, enabling a better comparison.

In each graph each point shows a mean value of 5 eyes. In the following Table 5, the blood pressures and the heart rates of subjected animals at the first day and the eighth day are shown in comparison to controls, when a 0.002 % and 0,02 % mabuterol-hydrochloride solution had been administered.

TABLE 5

|  | Control | 0.0002% mabuterol-hydrochloride solution | 0.002% mabuterol-hydrochloride solution |
|---|---|---|---|
| blood pressure (mmHg) at the first day | 89,6 + 5,7 | 90,0 + 3,2 | 99,0 + 6,0 |
| blood pressure (mmHg) at the eighth day | 87,0 + 2,5 | 87,0 + 4.6 | 94,0 + 4,0 |
| heart rate (beats/min) at the first day | 233,2 + 10,1 | 217,0 + 11,4 | 243,0 + 6,6 |
| heart rate (beats/min) at the eighth day | 243,0 + 5,8 | 230,0 + 8,8 | 233,0 + 5,4 |

EXAMPLE 7

Effect on ocular-mucous membrane

The obtained ophthalmic solutions, as described in Example 1, were subjected to the following test:

Acute repeated administration

Twelve male normal adult white rabbits having a body weight of 2,8 to 3,2 kg (Japanese white native species, 7 to 8 months old) were divided into 4 groups. In each group, 3 eyes were used.

50 μl of a phosphate buffer solution having a pH of 6,7 and containing 0,0002 %, 0,02 % or 2 % mabuterol-hydrochloride obtained according to Example 1 were exactly measured with a micropipette, and this solution was administered to one eye of 3 rabbits 9 times a day (every 1 hour) for three successive days.

With each concentration of the ophthalmic solution applied, no abnormality could have been found with regard to the external eye, its fundus and the pathological histology of the eyeball.

Administration for two successive weeks

Twelve male normal adult white rabbits having a body weight of 2,8 to 3,2 kg (Japanese white native species, 7 to 8 months old) were divided into 4 groups. In each group, 3 eyes were used.

50 μl of 0,0002 %, 0,002 % and 0,02 % mabuterol-hydrochloride ophthalmic solution obtained according to Example 1 were exactly measured with a micropipette. The solution was administered to each one eye of 3 rabbits 3 times a day (every 3 hours) for fourteen successive days. No external ocular abnormality could be found; the fundus and the pathological histology of the eyeball showed normal conditions.

Effect of the invention

The ophthalmic solution for intraocular pressure adjustment according to the present invention containing mabuterol as the active ingredient shows a strong effect in decreasing intraocular pressure, it is very effective as an ophthalmic solution for intraocular pressure adjustment for the treatment of ocular hypertension and glaucoma. Moreover, the ophthalmic solution shows no myosis action as it is the case with pilocarpine ophthalmic solutions, it is void of risks that would contraindicate it for asthmatic patients or that would give rise to bradycardia as is the case for ophthalmic solutions contaning β-recepor blocking agents.

Therefore, the ophthalmic solution of the present invention is clinically valuable as an ophthalmic solution for intraocular pressure adjustment for use in treating ocular hypertension and glaucoma.

Brief explanation of the drawings

FIG. 2a is a graph showing each intraocular pressure change with the lapse of time, in each case after application of an ophthalmic solution containing 0,0002 and 0,002 % of mabuterol and the control solution;

FIG. 4 is a graph showing each intraocular pressure change with the lapse of time in the cases of administering a 0,0002 %, 0,002 % and 0,02 % mabuterol-hydrochloride ophthalmic solution and a control solution at day one, FIG. 5 shows the changes at day ten.

FIGS. 6, 7 and 8 show the effects of ophthalmic solutions according to the invention on day one, day five and day ten.

FIG. 13 demonstrates blood pressure changes and heart rate changes in comparison to controls for the first and the eighth day after the administration of ophthalmic solutions according to the invention.

Figure 1:
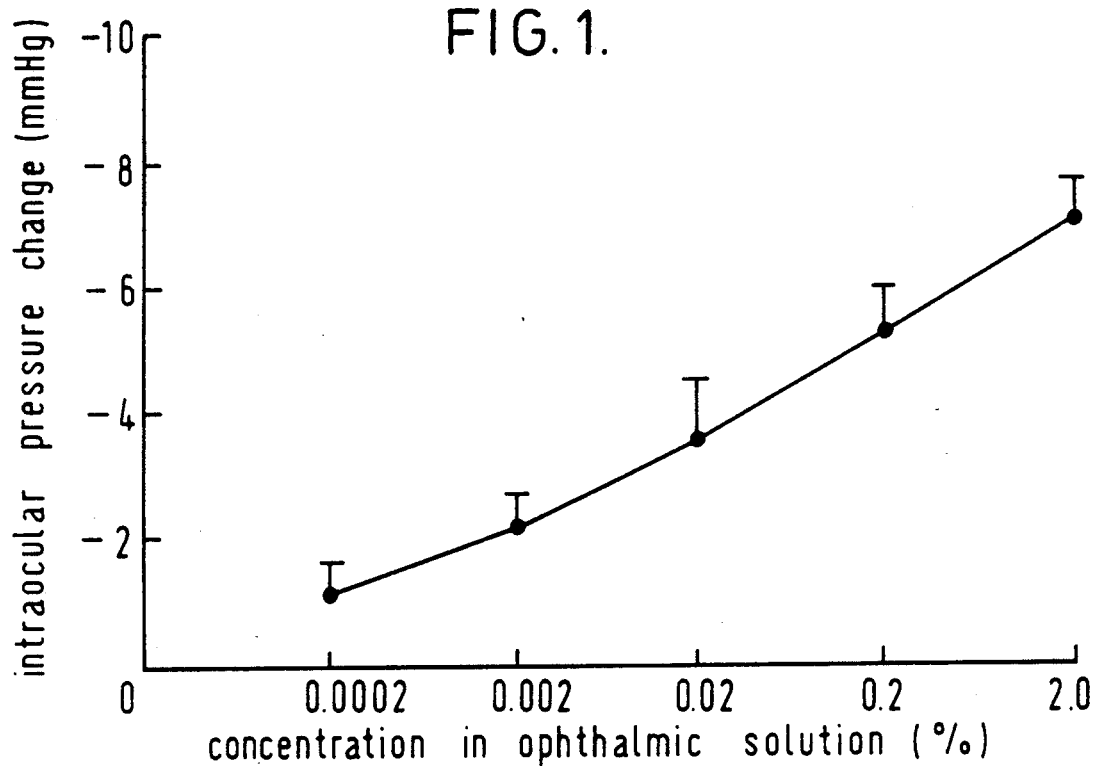
FIG. 1 is a graph showing a relation between the concentration of mabuterol hydrochloride in the ophthalmic solution (the concentration in the ophthalmic solution) and the intraocular pressure change after 1 hour from application of the ophthalmic solution.
Figure 3:
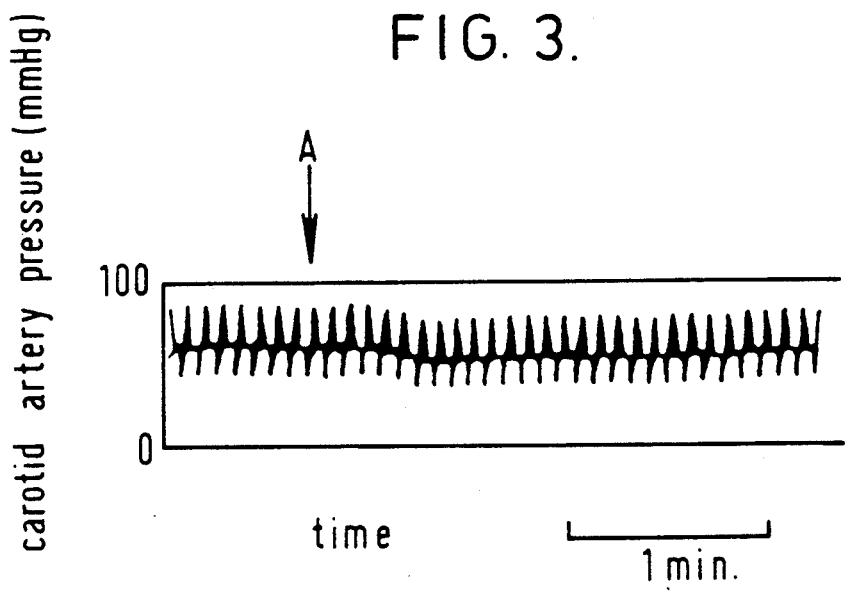
FIG. 3 is a sketch of a part of a chart showing carotid artery pressure change with the lapse of time when the mabuterol solution was intravenously administered.
Figure 2B:
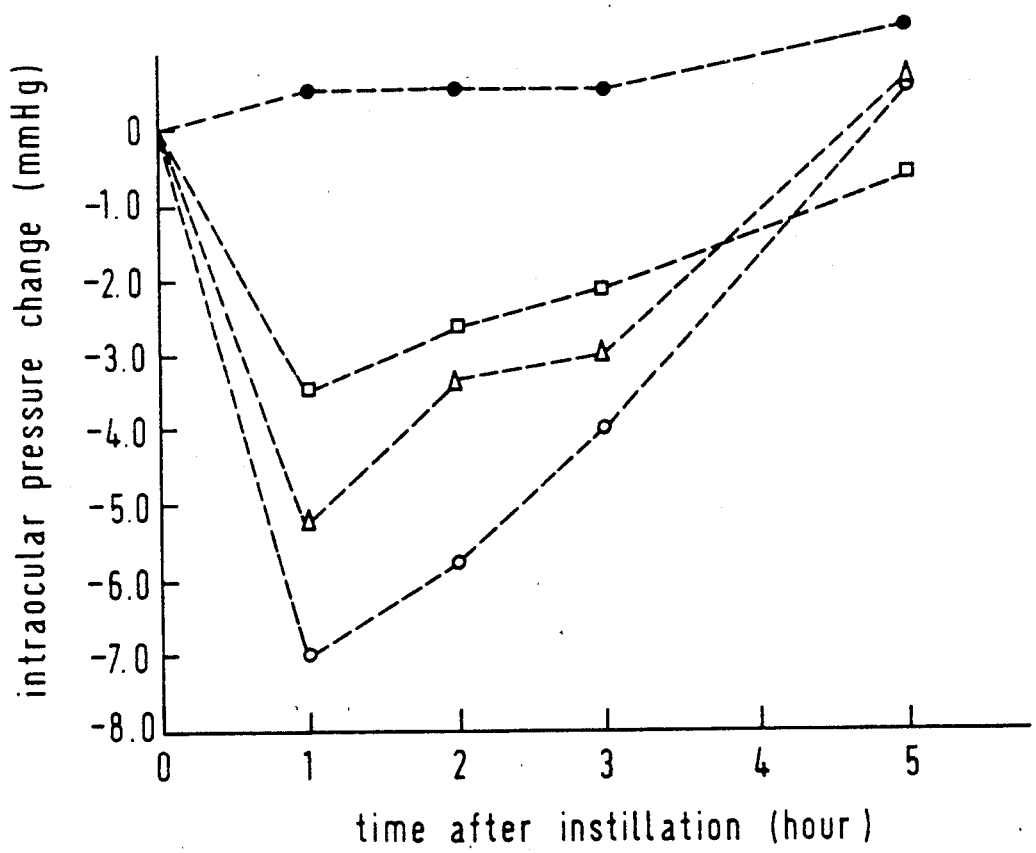
FIG. 2b is a graph showing each intraocular pressure change with the lapse of time, in each case after application of an ophthalmic solution containing 0,02, 0,2 or 2,0 % of mabuterol and the control solution.
Figure 9:
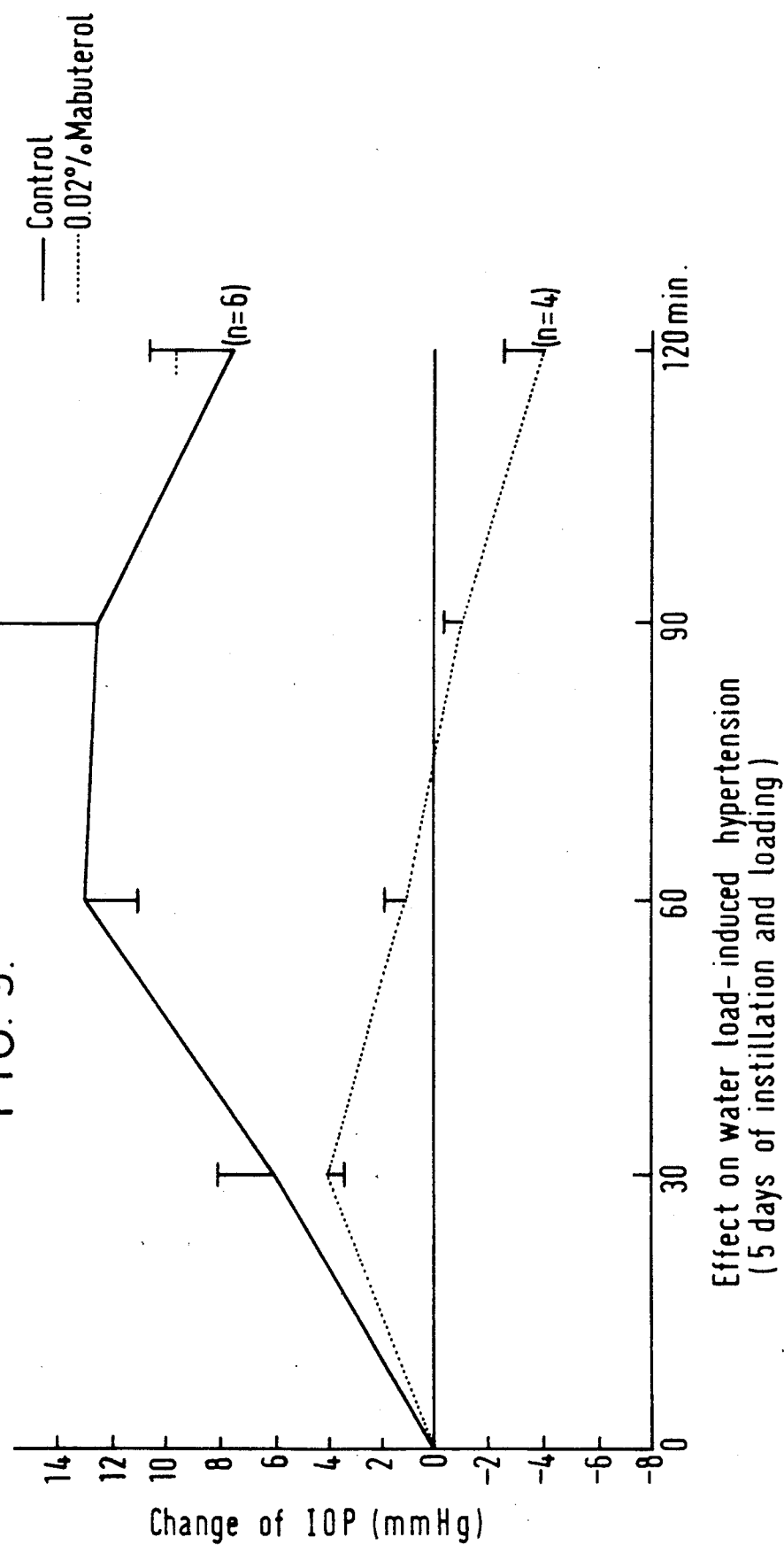
FIGS. 9 and 10 show the effects upon water-load induced hypertension at day five after 5 days of administration of an ophthalmic solution according to the invention and waterloading and accordingly at day ten (same conditions).
Figure 10:
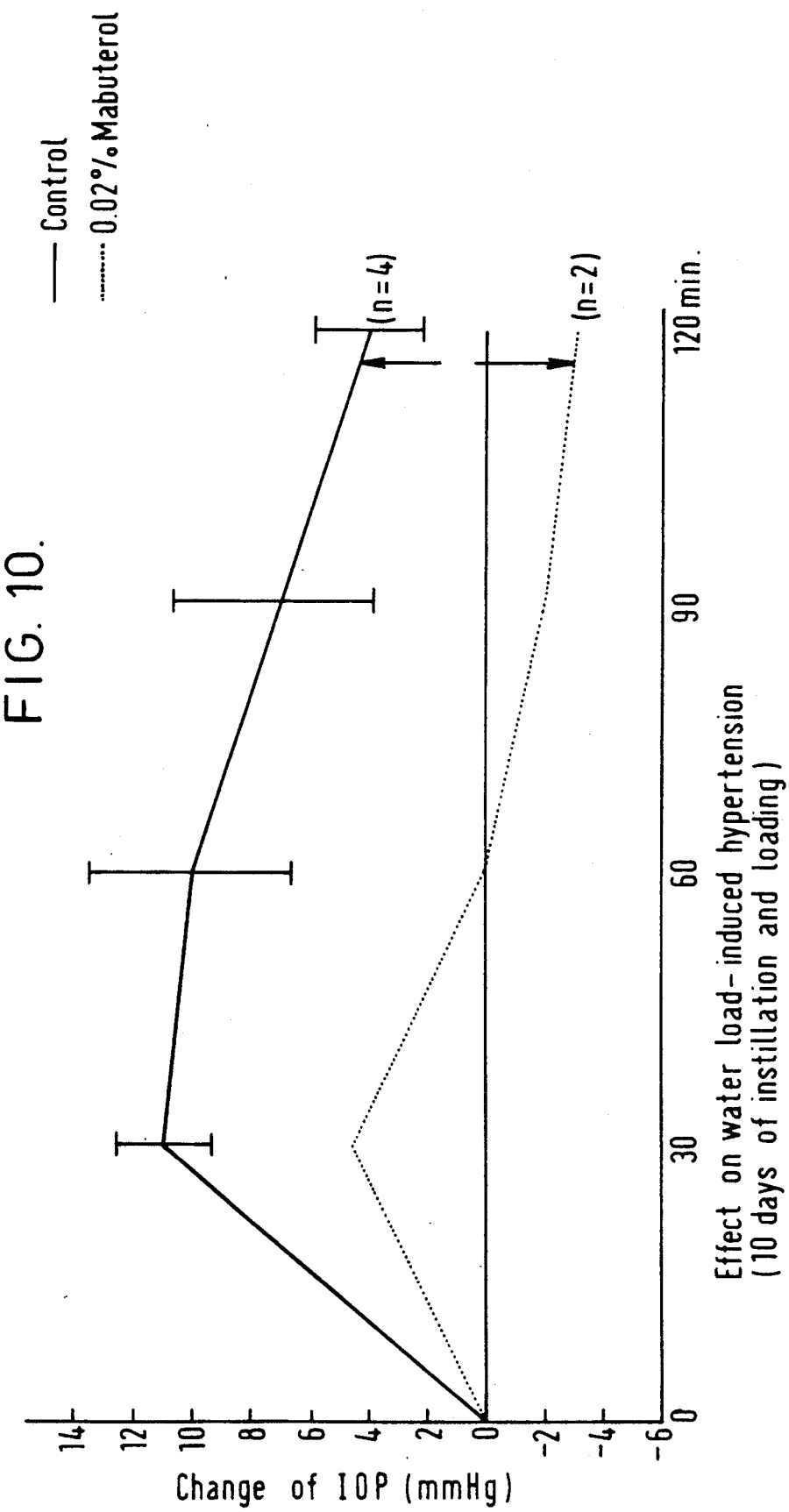
Figure 11:
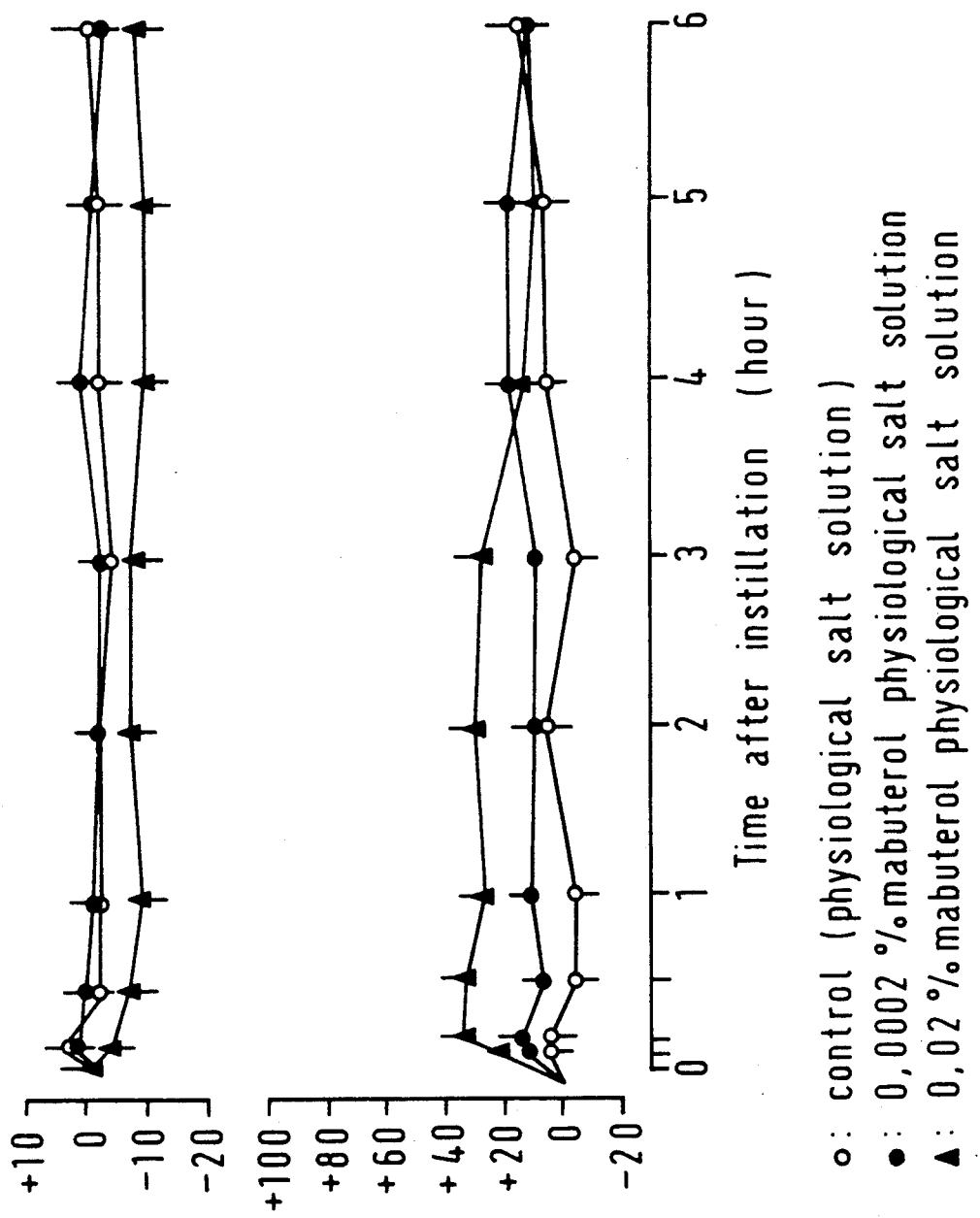
FIGS. 11 and 12 demonstrate the relation between time after administration of ophthalmic solutions according to the invention and heart rate and blood pressure, FIG. 11 at day one, FIG. 12 at day eight.
Figure 12:
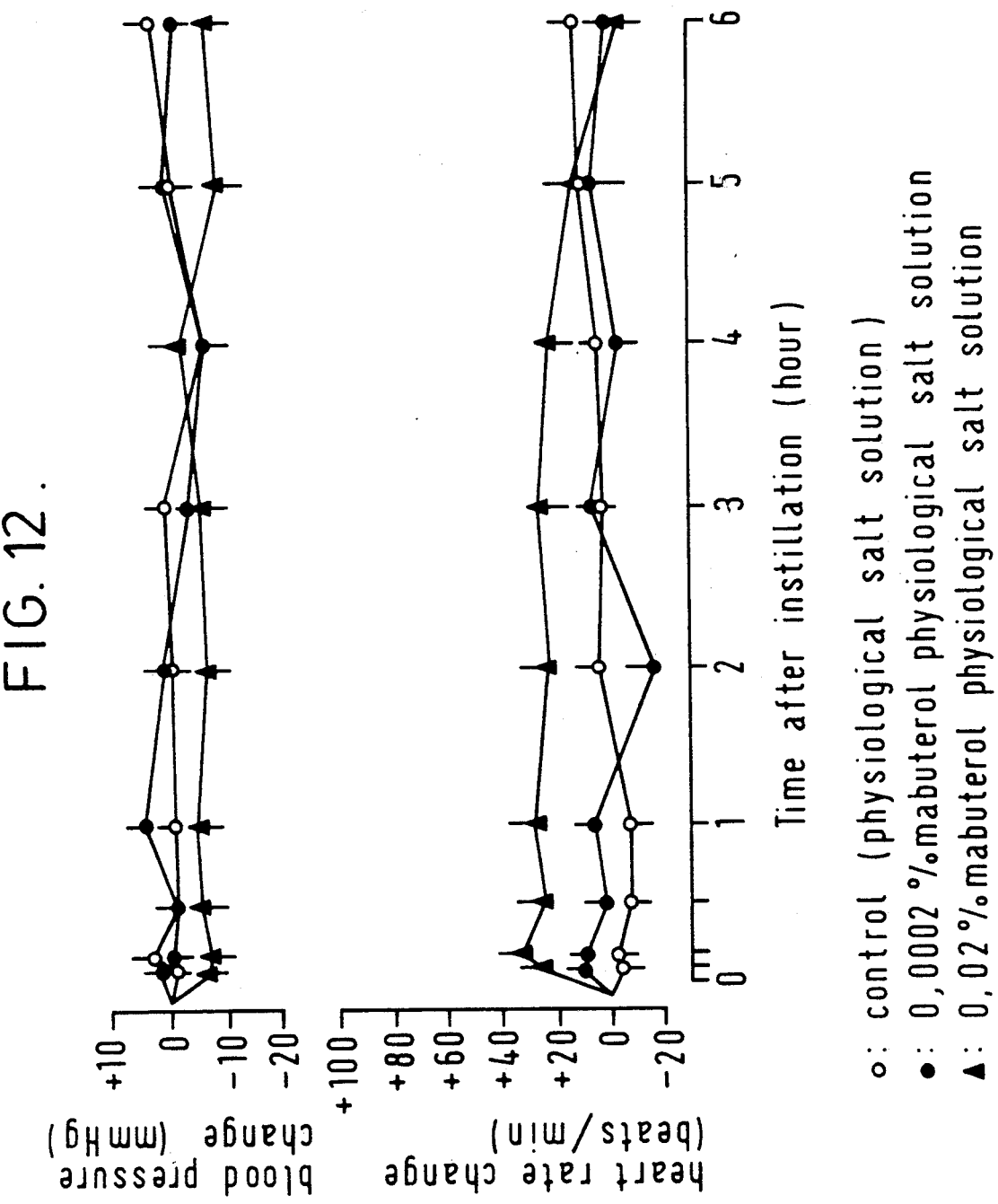

What we claim is:

1. A method for lowering intraocular pressure which comprises instilling into the eye an opthalmic solution comprising an intraocular pressuring lowering amount of a compound of the formula II

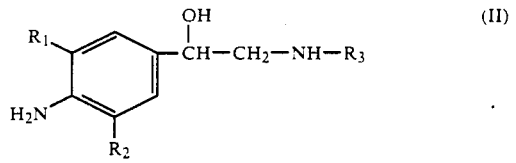

wherein
$R_1$ is hydrogen, fluorine, chlorine, bromine, iodine or cyano;
$R_2$ is fluorine, trifluoromethyl, nitro or cyano; and
$R_3$ is alkyl of 3 to 5 carbon atoms, hydroxyalkyl of 3 to 5 carbon atoms, cycloalkyl of 3 to 5 carbon atoms, 1-(3,4-methylenedioxy-phenyl)-2-propyl or 1-(p-hydroxy-phenyl)-2-propyl;
or a pharmaceutically acceptable salt thereof.

2. The method of claim 1 wherein the compound of formula II is 1-(4'-amino-3'-chloro-5'trifluoromethyl-phenyl-2-tert.-butylaminoethanol or a pharmaceutically acceptable salt thereof.

3. The method of claim 1 or 2 wherein the amount of the compound of formula II instilled is between about $1.10^{-6}$ and 2.0 mg.

* * * * *